United States Patent
Fois et al.

(10) Patent No.: US 11,261,138 B2
(45) Date of Patent: Mar. 1, 2022

(54) PROCESS FOR PRODUCING OLEFINS FROM ALCOHOLS

(71) Applicant: Versalis S.p.A., San Donato Milanese (IT)

(72) Inventors: Giovanni Antonio Fois, Borgo Virgilio (IT); Roberto Buzzoni, Chivasso (IT)

(73) Assignee: Versalis S.P.A., San Donato Milanese (IT)

( * ) Notice: Subject to any disclaimer, the term of this patent is extended or adjusted under 35 U.S.C. 154(b) by 0 days.

(21) Appl. No.: 16/628,052

(22) PCT Filed: Jul. 2, 2018

(86) PCT No.: PCT/IB2018/054900
§ 371 (c)(1),
(2) Date: Jan. 2, 2020

(87) PCT Pub. No.: WO2019/008499
PCT Pub. Date: Jan. 10, 2019

(65) Prior Publication Data
US 2021/0147316 A1  May 20, 2021

(30) Foreign Application Priority Data
Jul. 4, 2017  (IT) .......................... 102017000074911

(51) Int. Cl.
C07C 1/24 (2006.01)
C07C 37/08 (2006.01)
C07C 407/00 (2006.01)
C07C 29/145 (2006.01)

(52) U.S. Cl.
CPC .............. *C07C 1/24* (2013.01); *C07C 29/145* (2013.01); *C07C 37/08* (2013.01); *C07C 2529/70* (2013.01)

(58) Field of Classification Search
CPC .......... C07C 1/24; C07C 37/08; C07C 407/00
See application file for complete search history.

(56) References Cited

U.S. PATENT DOCUMENTS

| | | | |
|---|---|---|---|
| 3,832,449 A | 8/1974 | Rosinski et al. | |
| 4,552,739 A | 11/1985 | Kuhl | |
| 5,017,729 A | 5/1991 | Fukuhara et al. | |
| 5,227,563 A | 7/1993 | Fukuhara et al. | |
| 5,364,981 A | 11/1994 | Knifton et al. | |

FOREIGN PATENT DOCUMENTS

| | | |
|---|---|---|
| CN | 104549435 A | 4/2015 |
| CN | 104549436 A | 4/2015 |
| EP | 0 018 089 | 10/1980 |
| EP | 0 847 802 | 6/1998 |
| EP | 1 572 357 B1 | 9/2005 |
| WO | 2012/175601 A1 | 12/2012 |
| WO | 2013/017496 | 2/2013 |
| WO | 2015/056167 | 4/2015 |

OTHER PUBLICATIONS

International Search Report and Written opinion for PCT/ IB2018/054900, dated Sep. 7, 2018.
Reddy KSN et al., "Alkylation of benzene with isopropanol over zeolite beta", Applied Catalysis A: Gen, Elsevier, Amsterdam, NL, vol. 95, Jan. 1, 1993, pp. 53-63.
Klaus Weissermel and Hans-Jurgen Arpe, Industrial Organic Chemistry, 4th edition 2003, John Wiley & Sons, pp. 191-202.
"Propanols—Advances in Research and Application", Scholarly Briefs, Q. Ashton Acton editor (2013) Scholarly Editions, pp. 157-159.
Yu-Sin Jang, et al., "Bio-based production of C2—C6 platform chemicals" (2012), Biotechnology and Bioengineering, vol. 109, pp. 2437-2459.
E. M. Green, "Fermentative production of butanol—the industrial perspective" (2011), Curr. Opin. Biotechnol., vol. 22, pp. 337-343.
B.G. Hermann and M. Patel, "Today's and Tomorrow's Bio-Based Bulk Chemicals From White Biotechnology" (2007), Appl. Biochem. Biotechnol., vol. 136, pp. 361-388.
M. Zhang and Y. Yu, "Dehydration of Ethanol to Ethylene" (2013), Ind. Eng. Chem. Res., vol. 52, pp. 9505-9514.
R.J.J. Nel and A. de Klerk, "Dehydration of C5—C12 Linear 1-Alcohols over η-Alumina to Fuel Ethers" (2009), Ind. Eng. Chem. Res., vol. 48, pp. 5230-5238.
T.K. Phung, et al., "A study of commercial transition aluminas and of their catalytic activity in the dehydration of ethanol" (2014), J. Catal., vol. 311, pp. 102-113.

(Continued)

*Primary Examiner* — Sikarl A Witherspoon
(74) *Attorney, Agent, or Firm* — Praedcere Law

(57) ABSTRACT

The invention relates to a process for producing olefins from alcohols by means of catalytic dehydration. More in particular, the present invention relates to a process for producing at least one olefin by dehydrating at least one alcohol having a number of carbon atoms comprised between 2 and 6, preferably comprised between 2 and 4, more preferably at least one alcohol having a number of carbon atoms of 3, even more preferably 2-propanol, in the presence of a catalytic material comprising at least one large pore zeolite in acid form, or predominantly acid form, preferably selected from the group consisting of zeolites having BEA structure, MTW structure and mixtures thereof, and preferably at least one inorganic binder, more preferably alumina. Preferably, the olefin has the same number of carbon atoms as the starting alcohol. Furthermore, preferably the olefin does not contain conjugated double bonds and more preferably the olefin is a mono-olefin. Subject matter of the present invention is also the use of the aforementioned olefin in an alkylation process of aromatic hydrocarbons, in particular the use of propylene for alkylating benzene to provide cumene. The aforementioned cumene can be used in an integrated process for preparing phenol and acetone, in accordance with the Hock method, wherein acetone can be reduced to 2-propanol, to be recycled to the process of the invention to obtain propylene again.

18 Claims, No Drawings

(56) References Cited

OTHER PUBLICATIONS

V. Calsavara, N.R.C.F. Machado, J.L. Bernardi, Jr, and E.F. Sousa-Aguiar, "On the acidity and/or basicity of USY zeolites after basic and acid treatment" (2000), Braz. J. Chem Eng., vol. 17, pp. 91-98.

M. Hunger and T. Horvath, "Conversion of Propan-2-ol on Zeolites LaNaY and HY Investigated by Gas Chromatography and in Situ MAS NMR Spectroscopy under Continuous-Flow Conditions" (1997), J. Catal., vol. 167, pp. 187-197.

N. Zhan, Y. Hu, H. Li, D. Yu. Y. Han e H. Huang, "Lanthanum-phosphorous modified HZSM-5 catalysts in dehydration of ethanol to ethylene: A comparative analysis" (2010), Catal. Commun., vol. 11, pp. 633-637.

T.K. Phung, L. Proietti Hernández, A. Lagazzo and G. Busca in "Dehydration of ethanol over zeolites, silica alumina and alumina: Lewis acidity, Brønsted acidity and confinement effects" (2015), Appl. Catal. To: General, vol. 493, pp. 77-89.

E.T.C. Vogt et al.,"Beyond twelve membered rings" (2001), Studies in Surface Sci.and Catal., vol. 137, pp. 1003-1027.

J.V. Smith, "Definition of a zeolite" (1984), Zeolites, vol. 4, pp. 309-310.

"Atlas of zeolite Framework types" (2007), sixth edition edited by C. Baerlocher, L.B. McCusker and D.H. Olson, Elsevier).

"Molecular Sieves—Principles of Synthesis and Identification" (R. Szostak, Ed.) Second Edition 1998, International Thomson Publishing, pp. 31-33.

C. A. Emeis, "Determination of Integrated Molar Extinction Coefficients for Infrared Absorption Bands of Pyridine Adsorbed on Solid Acid Catalysts" (1993), J. Catal., vol. 141, pp. 347-354.

PROCESS FOR PRODUCING OLEFINS FROM ALCOHOLS

The invention relates to a process for producing olefins from alcohols by means of catalytic dehydration.

More in particular, the present invention relates to a process for producing at least one olefin by dehydrating at least one alcohol having a number of carbon atoms comprised between 2 and 6, preferably comprised between 2 and 4, more preferably at least one alcohol having a number of carbon atoms of 3, even more preferably 2-propanol, in the presence of a catalytic material comprising at least one large pore zeolite in acid form, or predominantly acid form, preferably selected from the group consisting of zeolites having BEA structure, MTW structure and mixtures thereof, and preferably at least one inorganic binder, more preferably alumina. Preferably, the olefin has the same number of carbon atoms as the starting alcohol. Furthermore, preferably the olefin does not contain conjugated double bonds and more preferably the olefin is a mono-olefin.

Subject matter of the present invention is also the use of the aforementioned olefin in an alkylation process of aromatic hydrocarbons, in particular the use of propylene for alkylating benzene to provide cumene. The aforementioned cumene can be used in an integrated process for preparing phenol and acetone, in accordance with the Hock method, wherein acetone can be reduced to 2-propanol, to be recycled to the process of the invention to obtain propylene again.

PRIOR ART

Olefins like ethylene, propylene and butylene are important intermediates or "building blocks" in the chemical industry. For example, ethylene is an important intermediate in the synthesis process of styrene, acetic acid, acetaldehyde, ethylene oxide, ethylene glycol, etc. and for obtaining polymers such as polyethylene, polystyrene and polyvinylchloride. Likewise, propylene can be used for example in the formulation of fuels, or for obtaining polypropylene, or in the synthesis processes of different compounds of industrial interest such as, for example, cumene, acrylonitrile, acrylic acid and propylene oxide. Finally, butylene and isobutylene are used, amongst other things, for producing fuel additives (e.g. methyl-t-butyl ether, MTBE, and iso-octane) and for obtaining polymers, copolymers and synthetic rubbers.

These so called "light" olefins are especially obtained by means of cracking hydrocarbons and in particular through steam cracking of supplies comprising natural gas or virgin naphtha. However, it is important to note that in this sector a transition has recently been recorded from fillers comprising heavy fractions, that allow benzene, butylene, propylene to be obtained, towards light feedstocks (e.g. ethane, propane, liquefied petroleum gas, LPG), particularly to promote the production of ethylene.

In any case, the reduction of oil reserves, on the one hand, and the increased sensitivity to issues regarding protection of the environment have pushed research increasingly towards alternative processes to cracking hydrocarbons and developing alternatives preferably based on the use of renewable sources.

From this perspective, obtaining olefins by dehydrating alcohols, of any origin, displays great development potential and wide application prospects, showing itself to be economically sustainable.

The alcohols that can be advantageously used for this purpose can be obtained from the transformation of classic chemical industry products, also allowing process integrations and product exploitations.

Alcohols that can be obtained through classic industrial synthetic processes can be prepared, for example, by hydrogenating carbonyl groups (e.g., 2-propanol from acetone), or by hydrating the corresponding olefins (e.g., ethanol from ethylene, propanol from propylene, sec-butanol from n-butene and tert-butanol from iso-butene), or with other methods known to a person skilled the art as reported, for example, in "Industrial Organic Chemistry", authors Klaus Weissermel and Hans-Jürgen Arpe, 4th edition 2003, John Wiley & Sons, pag. 191-202.

For example, a commonly used intermediate in the production of 1-propanol and 2-propanol is acetone. A list of patents relating to the hydrogenation of acetone to propanol can be found in "Propanols—Advances in Research and Application", *Scholarly Briefs*, Q. Ashton Acton editor (2013) Scholarly Editions, pag 157-159.

In turn, acetone can be produced through fermentation methods or through classic synthetic methods such as the phenol synthesis process according to Hock, which envisages the oxidation of cumene (generally prepared by alkylating benzene with propylene) to cumene hydroperoxide, which is decomposed to phenol and acetone.

If, on the one hand, the contemporary production of phenol and acetone in a single production unit certainly represents a positive aspect from an industrial point of view, the existence of an imbalance in the demand for the two products could, however, represent a commercial problem. In fact, it should be remembered that for every kg of phenol produced from cumene, 0.61 kg of acetone are also produced.

Considering, for example, that one of the main uses of acetone is the production of methyl methacrylate (MMA), the market demand for which is reducing, while the demand for Bisphenol A (BPA), phenolic resins and caprolactam, the main derivatives of phenol, is increasing, the problem deriving from excess acetone production, in the process for obtaining phenol via cumene, can be easily understood.

U.S. Pat. No. 5,017,729 describes a process for the production of phenol via cumene hydroperoxide characterized by the use of propylene, in the cumene preparation step, wherein said propylene is partially or totally deriving from the reduction of acetone (co-produced with phenol) with hydrogen to 2-propanol and the subsequent dehydration of the latter to propylene. In particular, in the process proposed in U.S. Pat. No. 5,017,729, a very expensive step is the dehydration step to propylene of the 2-propanol obtained by the reduction of acetone with hydrogen.

Although it is possible to obtain cumene, to be used in the aforementioned phenol synthesis process, by alkylating benzene directly with the 2-propanol obtained from the hydrogenation of acetone, it is clear that providing an economically viable process for dehydrating alcohol to olefin would have the immediate advantage of recirculating the propylene within a consolidated process.

For the olefin production process according to the present invention, it is also possible to use alcohols of biological origin, or from renewable sources, obtainable by fermentation or however by transforming materials of biological origin or by transforming materials obtained by fermentation (bio-alcohols).

Over recent years, many fermentation processes have been developed for the production of higher industrial alcohols such as isobutanol. The catalytic dehydration of alcohols of biological derivation for obtaining the corresponding olefins can generate positive margins and, according to the market price, can become as profitable if not more so than traditional petrochemical processes. This approach was described, for example, by Yu-Sin Jang, et al., in "Bio-based production of C2-C6 platform chemicals" (2012), *Biotechnology and Bioengineering*, vol. 109, pag. 2437-2459 (DOI: 10.1002/bit.24599).

In particular, propanols can also be obtained by hydrogenating bio-acetone, produced for example through the known process "Acetone-Buthanol-Ethanol" (ABE) described, for example, by E. M. Green, in 'Fermentative production of butanol—the industrial perspective" (2011), *Curr. Opin. Biotechnol.*, vol. 22, pag. 337-343 (DOI: 10.1016/j.copbio.2011.02.004) and by B. G. Hermann, and M. Patel, in "Today's and Tomorrow's Bio-Based Bulk Chemicals From White Biotechnology" (2007), *Appl. Biochem. Biotechnol.*, vol. 136, pag. 361-388 (DOI:10.1007/s12010-007-9031-9).

Classically, the production of olefins by dehydrating alcohols is obtained by treating the aforementioned alcohols with strong acids, such as sulfuric acid, phosphoric acid, perchloric acid or heteropolyacids such as phosphotungstic acid and phosphomolybdic acid. The use of catalysts based on strong acids imposes the use of reactors made of corrosion-resistant materials, and also implies the problem of the subsequent separation from the products and disposal of said acids. A person skilled in the art is also aware that, in the presence of strong acids, the olefins obtained tend to polymerize or isomerize, with the effect of reducing the yield of the desired product.

Heteropolyacids in particular have been used successfully in the conversion process of ethanol to ethylene, displaying high activity also at low operating temperatures. A disadvantage of heteropolyacids is their low heat stability, which requires delicate rejuvenation operations on the catalyst when, after a certain usage time, carbon residues have accumulated on its surface.

Alternatively, the dehydration can be performed in the presence of solid acid catalysts. Numerous examples of processes for obtaining olefins by dehydrating alcohols, for example mentioned by M. Zhang and Y. Yu in "Dehydration of Ethanol to Ethylene" (2013), *Ind. Eng. Chem. Res.*, vol. 52, pag. 9505-9514 (DOI: 10.1021/ie401157c), envisage the use of solid alumina-based catalysts, as such or in combination with other oxides including $MgO/SiO_2$ (catalyst "SynDol"), $Cr_2O_3$, $Mn_2O_3$ or $TiO_2$.

Solid alumina-based catalysts are relatively cheap, but their use must consider some specific operating requirements. For example, they require the space velocity to be low and the reaction temperature to be high. It has in fact been demonstrated that in dehydration processes in which the aforementioned solid acid catalysts are used, the balance between the acidity of the catalyst and the temperature at which the reaction is performed, which is actually endothermic, is very important.

On the one hand, the acidic characteristics of these catalysts make the olefins obtained by dehydrating the corresponding alcohols at temperatures up to about 300° C. subject to oligomerization and polymerization reactions; on the other hand, by increasing the process temperature to 450° C. and above, cracking reactions occur, which are the cause of the formation of undesired sub-products.

Furthermore, in industrial practice, it is of primary importance for the conversion of alcohol to olefin to take place with the maximum possible yield. In fact, the excess unreacted alcohol would otherwise have to be recycled to the dehydration reactor, making extra equipment necessary for recycling purposes and the related investment and operating costs. It is important to note that as the dehydration yield decreases and the recycling portion increases, together with the unreacted alcohol, significant quantities of impurities could also be recycled which, accumulating in the dehydration reactor, can actually harm the quality of the olefin obtained.

U.S. Pat. No. 5,227,563 describes a process for preparing propylene from acetone, comprising a hydrogenation step of acetone to 2-propanol and a dehydration step of alcohol in the presence of a γ-alumina based catalyst at temperatures comprised between 290° C. and 320° C., values at which good conversions and selectivity are obtained. In this case, the yields obtained are connected by the authors to a reduction in the content of alkaline metals in the catalytic material and a specific distribution of the pores of the γ-alumina based catalyst, obtained starting from pseudoboehmite.

This patent explains that in the dehydration reaction of 2-propanol to propylene it is preferable, in selectivity terms, to use alumina from pseudoboehmite as a catalyst, which has a lesser tendency, with respect to strong acid catalysts (such as silica-alumina, zeolites and solid phosphoric acids), to promote, at the temperatures required to activate the reaction, also the polymerization of propylene and the formation of sub-products.

On the other hand, R. J. J. Nel and A. de Klerk, in "Dehydration of $C_5$-$C_{12}$ Linear 1-Alcohols over η-Alumina to Fuel Ethers" (2009), *Ind. Eng. Chem. Res.*, vol. 48, pag. 5230-5238 (DOI: 10.1021/ie801930r) report that by dehydrating alcohols having a number of carbon atoms comprised between 5 and 12 on γ-alumina, in a fixed-bed reactor at 300° C., atmospheric pressure and a flow rate of 0.026 $mol \cdot h^{-1} \cdot g^{-1}$, low conversion and yields to olefin are obtained; in particular, in the case of 1-pentanol, selectivity to olefin of 69% and 30% to the corresponding ether are obtained and a conversion of 69%, despite the high temperature. An increase in temperature leads to an increase in the conversion and the selectivity to olefin and a reduction of selectivity to ether; however, values of conversion and selectivity to olefin (comprising any dimers) greater than 90% are only observed at a temperature equal to 350° C.

In dehydration reactions of alcohols to olefins, the use of transition aluminas, used by an expert in the art also as inorganic binders or supports, was described by T. K. Phung, et al., in "A study of commercial transition aluminas and of their catalytic activity in the dehydration of ethanol" (2014), *J. Catal.*, vol. 311, pag. 102-113. In this case the conversion and selectivity to ethylene is lower than has been described in the past. For example, a γ-alumina such as Versal™ 250 by UOP shows a total conversion of 2% and a selectivity to olefin of zero when the dehydration reaction is performed at 200° C., and also at 300° C. a conversion of 77.8% and a selectivity to ethylene of 47.6% are obtained. The use of HUSY type zeolites was described by V. Calsavara, N. R. C. F. Machado, J. L. Bemardi, Jr, and E. F. Sousa-Aguiar in "On the acidity and/or basicity of USY zeolites after basic and acid treatment" (2000), *Braz. J. Chem Eng.*, vol. 17, pag. 91-98 (DOI:10.1590/S0104-66322000000100008). In this article, the dehydration of 2-propanol in the presence of catalysts comprising acidic ultrastable Y zeolites, treated with strong bases (e.g. NaOH solutions), takes place with conversion yields greater than 90% only after the zeolites obtained have been further subjected to acidic treatment and however by performing the dehydration reaction at temperatures of less than 400° C., which, as mentioned, promote the establishment of secondary reactions.

A drawback encountered in the dehydration process of alcohols with zeolite catalysts having FAU structure is also the formation of carbon residues ("coke") which can obstruct access to the pores of the zeolites, dramatically reducing the activity thereof. The formation of coke was demonstrated, for example, through $^{13}$C MAS NMR using Y type zeolites by M. Hunger and T. Horvath in "Conversion of Propan-2-ol on Zeolites LaNaY and HY Investigated by Gas Chromatography and in Situ MAS NMR Spectroscopy under Continuous-Flow Conditions" (1997), *J. Catal.*, vol. 167, pag. 187-197 (DOI: 10.1006/jcat.1997.1562). Using the aforementioned catalysts, the authors report high conversions of 2-propanol at 120° C., but record the formation of sub-products such as acetone and di-isopropylether in quantities up to 2% and the presence of coke precursors already after 7 hours of running time, highlighting that the industrial applicability of these catalytic materials remains limited.

The accumulation of carbon residues is a known drawback also of the alcohol dehydration process which uses the zeolite H-ZSM-5, belonging to the MFI medium pore zeolite family, as a catalyst, particularly under the temperature conditions necessary for reaching high conversions and selectivity.

On the other hand, the demonstration of the capacity of H-ZSM-5 to catalyze the dehydration reaction of alcohols to olefins at temperatures comprised between 200 and 300° C., has led to numerous attempts being made to improve the characteristics of this zeolite catalyst.

For example, CN 104549436 (A) describes a dehydration method of 2-propanol to propylene in the presence of a catalyst comprising zeolite ZSM-5 in the acid form, prepared so that the $SiO_2$—$Al_2O_3$ ratio (Silica-Alumina Ratio, SAR) is comprised between 50 and 400, the particle size is comprised between 100 and 500 nm, the specific surface area is comprised between 160 and 350 $m^2/g$. It is important to note that, although the aforementioned zeolite allows propylene to be obtained through the dehydration of 2-propanol with high conversions and yields also at the temperature of 240° C., such conversion is however limited to a particularly low "Weight Hour Space Velocity" (WHSV), equal to 0.5 $h^{-1}$. On the other hand, to obtain the same conversion rate at higher WHSVs, for example of 2 $h^{-1}$, it is necessary to operate at much higher temperatures (280° C.). However, also in this case, the selectivity of the reaction to propylene is not greater than 98.7%.

To reduce the acidity of the catalyst, responsible for the poor stability and resistance to the formation of carbon residues, numerous formulations comprising the zeolite H-ZSM-5 have been described in the prior art. The aforementioned zeolite can be modified by adding metals such as zinc, nickel, etc., or phosphorus and/or lanthanum as described, for example, by N. Zhan, Y. Hu, H. Li, D. Yu. Y. Han e H. Huang in "Lanthanum-phosphorous modified HZSM-5 catalysts in dehydration of ethanol to ethylene: A comparative analysis" (2010), *Catal. Commun.*, vol 11, pag. 633-637 (DOI:10.1016/j.catcom.2010.01.011). In this latter case, a small addition of lanthanum to a H-ZSM-5 catalyst already modified with phosphorous through impregnation, is able to improve the catalytic characteristics and the resistance of the carbon residues of the catalytic material, allowing it to reach 250° C. with 72 hours of operating time but to the detriment of the conversion (97.4%) and the selectivity to ethylene (96.4%).

CN 104549435 (A) also describes a catalyst based on the zeolite ZSM-5 having SAR comprised between 50 and 400, particle diameter comprised between 100 and 500 nm and specific surface area comprised between 160 and 350 $m^2/g$, further modified through impregnation or ion exchange with salts of elements belonging to rare earths such as lanthanum, cerium or praseodymium. The aforementioned catalyst, tested in a catalytic dehydration process of 2-propanol to produce propylene, is shown to be more effective than the catalyst based on the same zeolite modified with Zn. Higher conversions than 99%, although with lower selectivity than 99%, at relatively high temperatures and low WHSVs, are however connected with the presence of nitrogen as a diluent, making this approach difficult to apply at industrial level.

Other families of zeolites have been used for the purpose of converting alcohols into olefins; for example, WO 2013/017496 describes the use of a catalyst that comprises a zeolite, preferably selected from the families of medium pore zeolites MFI, MTT, FER, MEL, TON, MWW, EUO, MFS, modified with phosphorous and optionally with a metal, preferably an alkaline earth metal or belonging to the rare earths, for example Mg, Ca, Sr, Ba, La, Ce, and subjected to steaming, for obtaining light olefins from the dehydration of alcohols. In WO 2013/017496 the dehydration of ethanol is performed starting from extremely diluted aqueous solutions of this alcohol, which complicates the heating and purification processes thereof and the disposal of the effluent streams. Furthermore, steaming and impregnation are used for preparing the catalytic material, hence complicating the preparation of the catalyst with these post-treatments. In addition to this, high conversion and selectivity values are reported when the temperature is equal to 380° C.

Finally, T. K. Phung, L. Proietti Hemtndez, A. Lagazzo and G. Busca in "Dehydration of ethanol over zeolites, silica alumina and alumina: Lewis acidity, Brønsted acidity and confinement effects" (2015), *Appl. Catal. To: General*, vol. 493, pag. 77-89, describe the use of zeolite catalysts belonging to the zeolite families H-MFI, H-BEA, H-FAU, H-FER and H-MOR, therefore including medium pore zeolites and large pore zeolites, in the dehydration reaction of ethanol to obtain ethylene. In the experimental conditions described, but characterized by a significant dilution of the organic substrate (7.9% by volume of ethanol in nitrogen with respect to the total volume of the filler), not appropriate for industrial application, all acidic zeolites have been shown to be more active than aluminas and silica-aluminas in converting ethanol to diethyl ether and ethylene.

Using zeolites H-FER and H-USY, a stable 99.9% yield to ethylene was obtained at 300° C. without deactivation for at least 405 min. At 200° C. instead, zeolites show a conversion of around 80% and a predominant selectivity to diethyl ether. The authors report good performance levels of large pore zeolites and substantial quantities of coke obtained on the surface of medium pore zeolites. It is also appropriate to report that, among large pore zeolites, those that have demonstrated the best activity for the production of ethylene from ethanol, under the conditions used, were zeolites with FAU structure and in particular the zeolite H-Y and the zeolite H-USY.

Also using zeolites with H-BEA structure, known to a person skilled in the art as large pore zeolites (described for example by E. T. C. Vogt, et al., in "Beyond twelve membered rings" (2001) *Studies in Surface Sci. and Catal.*, vol. 137, pag. 1003-1027 (DOI: 10.1016/S0167-2991(01)80264-0)), lower selectivity to ethylene was obtained and a tendency to form significant quantities of carbon residues (coke), which can reduce the durability of the catalyst.

In general, the cited studies demonstrated that in the dehydration process of alcohols, it is possible to use a zeolite as the catalyst, as long as it is modified, as in general zeolites can display greater activity than aluminas, however without modifications they are less stable. All the modifications described have however been evaluated exclusively at laboratory scale.

Since it is therefore clear that the known solutions are not free from drawbacks, such as the need to operate at high temperatures or in the presence of diluents, the low stability of the catalytic system over time, etc., the need remains to identify new catalytic systems, that are increasingly effective and resistant, that can be advantageously used in the dehydration reaction of an alcohol for producing an olefin.

It is therefore an object of the present invention to provide a process for obtaining olefins by dehydrating alcohols, preferably olefins having the same number of carbon atoms with respect to the starting alcohols, and preferably a process for preparing mono-olefins, even more preferably for preparing propylene by dehydrating 2-propanol, which is substantially free from the drawbacks highlighted above of the prior art and that, in particular, displays high conversions and selectivity at lower temperatures than reported in the art, using catalytic systems with high stability and process conditions that are easy to apply also on industrial scale.

The invention relates in particular to a process for producing at least one olefin by dehydrating at least one alcohol having a number of carbon atoms comprised between 2 and 6, preferably comprised between 2 and 4, more preferably having a number of carbon atoms of 3, performed in the presence of a catalytic material, which comprises at least one large pore zeolite in acid form or predominantly acid form, selected from the group consisting of zeolites having BEA structure, MTW structure and mixtures thereof, and preferably at least one inorganic binder, more preferably alumina.

In a preferred aspect, the olefin has the same number of carbon atoms as the starting alcohol; furthermore, preferably the olefin is a mono-olefin.

In a particularly preferred aspect, said alcohol is 2-propanol and the olefin obtained is propylene.

Furthermore, in a particularly preferred aspect, said catalytic material comprises a large pore zeolite in acid form, or predominantly acid form, belonging to the family of zeolites with MTW structure and even more preferably said zeolite is ZSM-12.

The large pore zeolite in acid or predominantly acid form comprised in the catalytic material used in the process of the invention, can be used in various forms, for example as such, usually in powder form with fine and uncontrolled particle size, or it may be "formed", operating according to any one of the forming processes known in the art such as, for example, extrusion, spherudizing, tableting, granulation, and the like. In the forming processes, the zeolite is normally combined with a so-called "binder", comprising a compound or a composition adapted to stabilize the desired final form of the solid without significantly altering the catalytic properties of the zeolite itself.

Preferably, the aforementioned zeolite can be used in extruded form. Furthermore, as mentioned, preferably said zeolite is formed in the presence of a binder, usually an inorganic oxide or a precursor thereof, such as alumina ($Al_2O_3$), silica ($SiO_2$), zirconium oxide ($ZrO_2$), titanium oxide ($TiO_2$), more preferably silica or alumina and even more preferably alumina. As well as said traditional binders, for forming zeolites, further chemical agents can also be added; prior to extrusion, for example, it is possible to also add a peptizing agent to the active phase, which can be mixed with said active phase of the catalytic material and with the binder, until a uniform paste is obtained. At the end of the forming processes, the material obtained is preferably subjected to calcination.

For the purpose of the present invention, the process for producing olefins of the present invention can be realized in gaseous phase or in mixed liquid/gaseous phase, preferably in gaseous phase, discontinuously (e.g. in an agitated and heated autoclave) or continuously (e.g. in one or more catalytic reactors in series), preferably continuously. The aforementioned catalytic material has been shown to be effective and selective, further characterized by physical and mechanical properties that allow simple and cheap reactor solutions to be chosen, for example based on fixed bed catalytic reactors. Furthermore, the catalytic material allows the process to be conducted with high space velocities; it has also been shown to tolerate particularly long running times without showing any significant performance losses, also in the absence of diluents and at low temperatures.

The process according to the present invention is characterized in particular in that it allows high yields of olefins to be obtained from the dehydration of alcohols, preferably propylene starting from 2-propanol, even operating at relatively low temperatures, promoting the containment of operating energy costs.

The invention further relates to the use of the olefin obtained through the aforementioned conversion process through the alkylation of an aromatic hydrocarbon, and preferably relates to the use of propylene obtained through the aforementioned process by alkylating benzene and obtaining cumene. The cumene thus produced can in turn by used for producing phenol through the Hock process and acetone as a co-product. Said acetone, after being separated from phenol, can be in turn advantageously subjected to hydrogenation to produce 2-propanol, which can be fed again to the process of the present invention, with a clear economic advantage connected with the recycling of said co-product.

Further characteristics and advantages of the present invention will become clear from the following detailed description.

For the purpose of the present description and following claims, the definitions of the numeric ranges always include the extremes unless specified otherwise.

In the description of the embodiments of the present invention, the use of the terms "comprising" and "containing" indicates that the options described, for example regarding the steps of a method or of a process or the components of a product or of a device, are not necessarily all-inclusive. It is however important to note that the present application also relates to the embodiments in which the term "comprising" in relation to the options described, e.g. regarding the steps of a method or of a process or the components of a product or of a device, must be interpreted as "which essentially consists of" or "which consists of", even if this is not explicitly stated.

For the purpose of the present invention, the term "substantially absent" or "substantial absence", when referred to a substance or a compound, means that said substance or compound is absent or present in negligible amounts.

For the purpose of the present description and following claims, the percentages are always by weight, except in cases in which it is specified otherwise.

For the purpose of the present description and the following claims, "zeolite" generally means a hydrated aluminosilicate of alkaline metals and alkaline earth metals whose crystalline structure is based on a three-dimensional framework of tetrahedrals $TO_4$ (where T=Si or Al), joined together through the oxygen atoms, generating a set of interconnected empty spaces and channels, occupied by cations and by molecules of water, which confer peculiar controlled porosity characteristics to the zeolite. Further properties of a zeolite are reported by J. V. Smith in "Definition of a zeolite" (1984), *Zeolites*, vol. 4, pag. 309-310. Zeolites differ from each other, amongst other things, according to the size of the channels present in their crystalline structure, and in particular the size of the rings, formed by the T atoms defined above, which delimit the space of said channels, and the extension of said channels in one, two or three dimensions in space, the interconnection of the channel system and the presence of cages at the intersection of the channels or along them (as described, for example, in "Atlas of zeolite Framework types" (2007), sixth edition edited by C. Baerlocher, L. B. McCusker and D. H. Olson, Elsevier). As is known, due to its ability to promote interaction between the constituents of a reaction mixture, a zeolite may represent the active phase of numerous catalysts.

For the purpose of the present description and the following claims, "large pore zeolites" means zeolites characterized by pores that are delimited by rings constituting a maximum of 12 T atoms (where T=Si or Al), according to a classification known to a person skilled in the art reported, for example, in "Molecular Sieves—Principles of Synthesis and Identification" (R. Szostak, Ed.) Second Edition 1998, International Thomson Publishing, pag. 31-33. An example of a large pore zeolite is zeolite ZSM-12, of the family having MTW structure.

Likewise, and with reference to the same classification, for the purpose of the present description and following claims, "medium pore zeolites", means zeolites characterized by pores delimited by rings constituting 10 T atoms (where T=Si or ll). An example of a medium pore zeolite is ZSM-5, of the MFI zeolite family.

For the purpose of the present description and the following claims, a zeolite is defined as being "in acid form" when at least 80% of the cation sites present on the crystal lattice of said zeolite are occupied by hydrogen ions, or "predominantly in acid form", when at least 50% of the cation sites present in its structure are occupied by hydrogen ions.

The acidity of a zeolite may be determined with any of the methods known to a person skilled in the art. For example, it can be measured by placing the catalytic material in contact with a base, for example pyridine, as described, for example, by C. A. Emeis, in "Determination of Integrated Molar Extinction Coefficients for Infrared Absorption Bands of Pyridine Adsorbed on Solid Acid Catalysts" (1993), *J. Catal.*, vol. 141, pag. 347-354.

In order for the hydrogen ion to substitute the metal cation present in the zeolite at the end of the synthesis, said zeolite is preferably subjected to ion exchange with ammonium ions, washing and subsequent calcination, in accordance with methods known to a person skilled in the art.

When the catalytic material used in the process of the present invention comprises at least one zeolite of the MTW family, in particular the zeolite ZSM-12, it is preferably used in the form in which at least 50% of the cation sites present in the structure of the zeolite are occupied by hydrogen ions, more preferably at least 80% of the cation sites are occupied by hydrogen ions, even more preferably at least 90% of the cation sites are occupied by hydrogen ions.

For the purpose of the present description and the following claims, the expression "specific surface area" indicates the BET specific surface area (measured according to the Brunauer, Emmett and Teller method) determined as known to a person skilled in the art, for example through the static absorption of nitrogen ($N_2$) at the liquid nitrogen temperature of −196.15° C. (77 K), e.g. using a Micromeritics ASAP 2010 instrument, in conformity with a standard method, e.g. ASTM D3663-03 (2008), known to a person skilled in the art.

For the purpose of the present description and the following claims, the XRD characterization (X-Ray Diffractometry) is performed as known to a person skilled in the art, for example with a Philips X'Pert Θ/2Θ automatic diffractometer with Bragg-Brentan geometry using a Cu-Kα Z-ray source with λ=1.5416 and a power of 1.6 kW.

For the purpose of the present description and the following claims, the "SAR ratio" of a zeolite means the $SiO_2/Al_2O_3$ molar ratio ("Silica Alumina Ratio", SAR) characteristic of the main constituents of the matrix of said zeolite.

The SAR ratio of a zeolite influences its chemical and physical characteristics, in particular the characteristics connected with the number and force of the acid sites.

The SAR ratio can be determined through elementary analysis of the zeolite, for example through WD-XRF ("Wavelength Dispersion X-Ray Fluorescence"), with a PANanalytical Axios Advanced spectrometer equipped with a 4 kW X-ray tube with a rhodium anode. In any case, for the purpose of the present description and the following claims, the SAR ratio always refers to the zeolite alone, regardless of any presence, in the catalytic material that comprises it, of inorganic binders and/or additional additives for the forming of said zeolite.

DETAILED DESCRIPTION OF THE INVENTION

The present invention relates to a process for preparing at least one olefin by dehydrating at least one alcohol having a number of carbon atoms comprised between 2 and 6, preferably between 2 and 4, even more preferably having a number of carbon atoms of 3, in the presence of a catalytic material comprising at least one large pore zeolite in acid form or predominantly acid form.

The process according to the present invention may be realized by placing in contact at least one alcohol having a number of carbon atoms comprised between 2 and 6, preferably between 2 and 4, even more preferably having a number of carbon atoms of 3, with a catalytic material comprising at least one large pore zeolite in acid form or predominantly acid form, to obtain at least one olefin.

The catalytic material is preferably formed, most preferably formed, in the presence of at least one inorganic binder.

The aforementioned large pore zeolite in acid form, or predominantly acid form, constitutes the active phase of said catalytic material.

In a preferred aspect, said zeolite is selected from the group consisting of zeolites having BEA structure, MTW structure, and mixtures thereof.

In a further preferred aspect, said large pore zeolite in acid form, or predominantly acid form, is selected from the group comprising zeolites having BEA structure.

Furthermore, the zeolite having BEA structure is characterized by a SAR comprised between 15 and 60 and more preferably comprised between 20 and 30.

Preferably the zeolite having BEA structure may be a zeolite Beta described, for example, in U.S. Pat. No. 3,308,069.

In accordance with U.S. Pat. No. 3,308,069, the composition of the zeolite Beta can be represented, in terms of molar ratio of oxides, as follows:

where x may have a value from 0 to 1, y is comprised between 5 and 100, w is less than or equal to 4, M is a metal ion such as sodium, n is the valency of the metal ion M, TEA is the tetraethylammonium ion.

In a second preferred aspect, said large pore zeolite in acid form, or predominantly acid form, is selected from the group comprising zeolites having MTW structure.

Furthermore, said zeolite having MTW structure is characterized by a SAR comprised between 40 and 200 and more preferably comprised between 70 and 150.

Preferably the aforementioned zeolite having MTW structure may be a ZSM-12 zeolite described, for example, in U.S. Pat. No. 4,552,739.

In accordance with U.S. Pat. No. 4,552,739, the composition of the zeolite ZSM-12 can be represented, in terms of molar ratio of oxides, as follows:

where M is at least one cation having valency n, X can vary from 20 to infinity and z can vary from 0 to 60.

Zeolite ZSM-12, and the different synthesis methodologies thereof are described in the prior art, for example in U.S. Pat. No. 3,832,449 and in EP 0 018 089.

Preferably, the olefin obtained with the process according to the present invention does not contain conjugated double bonds and more preferably said olefin is a mono-olefin, i.e. an olefin containing only one double bond.

Furthermore, the olefin preferably has the same number of carbon atoms as the starting alcohol.

Specific examples of alcohols that are particularly useful for the purpose of the present invention are: ethanol, 1-propanol, 2-propanol, 1-butanol, 2-butanol, iso-butanol, tert-butanol, 1-pentanol, 2-pentanol, 3-pentanol, isoamyl alcohol, 2-methyl-1-butanol, 1-hexanol, 2-hexanol, 3-hexanol, 2,3-dimethyl-1-butanol, 3-methyl-1-pentanol.

In a further preferred aspect, the starting alcohol is a propanol, even more preferably 2-propanol.

Preferably, said 2-propanol derives from the hydrogenation of acetone.

As mentioned, the large pore zeolite, in acid form, or predominantly acid form, used in the process according to the invention, can be formed in the presence of at least one inorganic binder.

The aforementioned inorganic binder can comprise a material conventionally used as a binder for catalysts. Non-limiting examples of inorganic binders can comprise, for example, silica, alumina, silica-alumina, zirconium oxide, titanium oxide, anionic and cationic clays, saponite, gibbsite, bentonite, kaolin, sepiolite, hydrotalcite, or mixtures thereof. In a preferred aspect, the inorganic binder is selected from the group comprising silica, alumina, silica-alumina and mixtures thereof and more preferably is alumina. Also preferred is an alumina-precursor binder, even more preferably γ-alumina. As is known to a person skilled in the art, γ-alumina can derive from calcination of pseudoboehmite or boehmite (as described, for example, by the already mentioned T. K. Phung, et al., in "A study of commercial transition aluminas and of their catalytic activity in the dehydration of ethanol" (2014), *J. Catal.*, vol. 311, pag. 102-113), which is also available commercially with the name Versal™.

The aforementioned inorganic binder is present in quantities such as to produce a catalytic material in which the weight ratio between zeolite and binder, in terms of relative quantity ranges is comprised between 95:5 and 5:95, preferably between 20:80 and 80:20, even more preferably between 35:65 and 65:35.

In order to facilitate the forming operations of the catalytic material, it is possible to add to said large pore zeolite in acid form, or predominantly acid form, and to said at least one inorganic binder, at least one peptizing agent preferably selected from aqueous solutions of: acetic acid, nitric acid, ammonium hydroxide. Said peptizing agent can be mixed with said zeolite and with the inorganic binder prior to forming, until a uniform paste is obtained, in accordance with methodologies known to a person skilled in the art.

To improve the rheological characteristics of the catalytic material, during the forming step it is possible to add one or more additives. These additives may preferably comprise: starches, cellulose or derivatives thereof, stearates, glycols, surfactants, or a mixture thereof.

For applications in fixed bed or fluidized bed reactors, the forming of the catalytic material in the presence of at least one inorganic binder is fundamentally important in order for the catalyst to maintain its physical integrity during use.

The large pore zeolite in acid form, or predominantly acid form, used in the process of the present invention can be subjected to forming according to any one of the methods known to a person skilled in the art, for example extrusion, spherudizing, tableting, granulation, and the like, in the presence of an inorganic binder, operating as described, for example, in EP 0 847 802 or in WO 2015/056167 A1, all by the Applicant and the contents of which are included here for reference purposes.

At the end of the forming step, the catalytic material may be in different forms, for example such as spheres, microspheres, granules, pellets, extruded cylindrical, three-lobe, four-lobe forms, etc. and may possibly be subjected to calcination. In a particularly preferred aspect, said catalytic material is in pellet form having a diameter that ranges from 1 to 6 mm, preferably from 1.5 to 5 mm and a length that ranges from 1 to 50 mm.

The aforementioned calcination can be performed in a muffle furnace, at a temperature comprised between 250° C. and 1200° C., preferably comprised between 450° C. and 800° C., for a time comprised between 1 hour and 36 hours, preferably comprised between 2 hours and 24 hours, even more preferably comprised between 4 hours and 18 hours. Said possible calcination can be performed in air, or in the presence of an inert gas (e.g. nitrogen), and is preferably performed in air.

The process for preparing an olefin by dehydrating an alcohol in accordance with the present invention can be performed at a temperature comprised between 100° C. and 300° C., preferably comprised between 150° C. and 250° C. and more preferably comprised between 175° C. and 220° C.

In a particularly preferred aspect of the invention, the aforementioned process is performed at a temperature comprised between 180° C. and 210° C.

Furthermore, said process can be conducted at a pressure comprised between 0.01 and 2 kPa, more preferably comprised between 0.05 and 1.5 kPa, even more preferably comprised between 0.08 and 0.5 kPa. In a particularly preferred aspect of the invention, said process is realized at a pressure comprised between 0.09 and 0.2 MPa.

Therefore, in a particularly preferred aspect of the invention, said process can be realized at a temperature comprised between 180° C. and 210° C., at a pressure comprised between 0.09 MPa and 0.2 MPa.

In a further preferred aspect said process can be performed in gaseous phase or in mixed liquid/gaseous phase, and more preferably is performed in gaseous phase.

The process of the present invention can be preferably carried out in the substantial absence of any solvent or inert diluent. In particular, it is preferably carried out in the substantial absence of an aromatic compound.

The process of the present invention can be realized continuously (e.g. in one or more catalytic reactors in series) or discontinuously (e.g. in a heated and agitated autoclave) and is preferably realized continuously.

Said process may be conducted in any type of reactor, preferably in a fixed bed reactor, a moving bed reactor or in a fluidized bed reactor.

In a preferred aspect of the present invention, said process can be performed in a fixed bed reactor. In this case, the catalytic material may be maintained in a single bed or split into various beds.

The reactor layout may comprise the recycling of part of the reaction effluents or of the catalytic material, in a "recirculation" reactor configuration.

In a further preferred aspect, when the process of the present invention is performed in mixed liquid/gaseous phase, and therefore there is a liquid phase present one or more Continuous flow Stirred Tank Reactors (CSTRs) can be used, containing the catalytic material in dispersion.

The process according to the present invention can also be performed continuously in a reactor configuration envisaging at least two reactors in parallel, preferably two fixed bed reactors in parallel, in which, when one reactor is operating, the catalytic material can be regenerated in the other reactor.

When the process is conducted continuously, in the temperature and pressure conditions specified above, the WHSV (Weight hourly space velocity), i.e. the ratio between the quantity by weight of reagent fed to the reactor and the quantity by weight of catalyst in the reactor itself, may be comprised between 0.5 $h^{-1}$ and 10 $h^{-1}$, is preferably comprised between 0.7 $h^{-1}$ and 7 $h^{-1}$ and even more preferably is comprised between 0.7 $h^{-1}$ and 4 $h^{-1}$. In a particularly preferred aspect, the WHSV is comprised between 0.8 and 3 $h^{-1}$.

The olefins produced with the process of the present invention are mainly used as intermediates in the synthesis processes of different compounds of industrial interest, and for obtaining polymers.

In particular, the olefins obtained through the aforementioned process can be used for alkylating aromatic hydrocarbons.

When the olefin obtained through the aforementioned process is propylene, said propylene may be used for alkylating benzene and obtaining cumene. The cumene thus produced can in turn be used for producing phenol through the Hock process, known to a person skilled in the art, and acetone as a co-product. Said acetone, after being separated from phenol, can be in turn advantageously subjected to hydrogenation to produce 2-propanol, which can be fed again to the process of the present invention.

Therefore, the subject matter of the invention is a process for producing propylene by dehydrating 2-propanol, performed in the presence of a catalytic material that comprises at least one large pore zeolite in acid form, or predominantly acid form, selected from the group comprising zeolites with BEA structure, MTW structure and mixtures thereof, preferably formed in the presence of at least one inorganic binder, where said 2-propanol derives from the hydrogenation of acetone obtained as a co-product of the synthesis of phenol through the Hock process.

The present invention finally relates to an integrated process for producing phenol which comprises the following steps:
(a) converting 2-propanol to propylene, by using the process for preparing at least one olefin by dehydrating at least one alcohol according to the present invention, as described above;
(b) alkylating benzene with the propylene obtained in step (a) to obtain cumene, in the presence of a catalytic material comprising at least one large pore zeolite in acid form, preferably with BEA structure;
(c) oxidizing the cumene obtained in step (b) with the formation of cumyl hydroperoxide;
(d) treating the cumyl hydroperoxide with acids to obtain a mixture of phenol and acetone;
(e) separating phenol from acetone;
(f) hydrogenating the acetone separated in step (e) to obtain 2-propanol, which is at least partially recycled to step (a).

For the purpose of the invention "at least partially recycled" means an amount comprised between 50% and 100% of the total amount of 2-propanol fed to step (a) of the process described above, the complement to 100% being comprised of fresh 2-propanol.

EXAMPLES

For the purpose of putting the present invention into practice and illustrating it more clearly, below are some non-limiting examples.

Example 1 in Accordance with the Invention
(Preparation of Catalytic Material Comprising Zeolite ZSM-12)

2.4 g of sodium aluminate (56% $Al_2O_3$) were dissolved in 84 g of an aqueous solution of 35% by weight tetraethylammonium hydroxide. The clear solution thus obtained was mixed with 200 g of Ludox® HS 40 colloidal silica in a 40% by weight suspension. After mixing, a uniform and clear gel was obtained, which was inserted into an AISI 316 steel autoclave equipped with an anchor stirrer. The gel was left to crystallize in hydrothermal conditions at 160° C. for about 70 hours. At the end, after cooling, the solid phase was separated from the mother liquor from the suspension obtained by filtration. The aforementioned solid phase was subjected to washing with demineralized water until washing water was obtained having a pH less than 9.

The solid was then subjected to calcination at 550° C. in air atmosphere, for 5 hours. The solid obtained was dispersed in an aqueous solution of ammonium acetate. The concentration of ammonium acetate in the solution was selected so that the molar ratio between ammonium ions and aluminum present in the dispersed solid was greater than or equal to 5. The solid was recovered through filtration and washed with demineralized water. The ion exchange process with the ammonium acetate solution and washing with demineralized water was repeated a second time. At the end, the solid was separated from the aqueous phase and placed to dry in an oven at 100° C. for 3 hours, in air atmosphere. A zeolite in ammonium form is obtained, containing residual sodium less than 50 ppm. The X-Ray Diffraction (XRD), performed by applying methodologies known to a person skilled in the art, confirmed the presence of a single crystalline zeolite phase characteristic of the MTW structure, while the chemical analysis of the material allowed the SAR of zeolite to be determined, which was equal to 99. Different preparations of zeolite performed according to the process described were mixed together so as to obtain a sample having uniform structural, morphological and compositional characteristics. 545 g of zeolite in ammonium form prepared in accordance with the protocol indicated above, were mixed with 600 g of Versal™ 150 pseudoboehmite in a planetary mixer for 30 minutes for the purpose of obtaining uniform distribution of the powders.

At the end, 300 mL of a 2% by weight acetic acid solution was added over 30 minutes to the mixture of powders, while mixing constantly. After the addition, the pasty mixture was unloaded from the mixer and transferred into a roller extruder equipped with a draw-plate with holes having a 2 mm diameter. The catalytic material was extruded in the form of pellets having a diameter of about 2 mm and a length of about 10 mm. The material was subsequently calcinated in air atmosphere for 2 hours at 350° C. and subsequently for another 3 hours at 550° C. After calcination, an extrusion of zeolite and alumina (gamma) is obtained with a mutual weight ratio of 55:45, determined based on the weight loss at 550° C. of the starting components, in which the zeolite is in acid form.

The final catalytic material thus obtained has a surface area of 246 m$^2$/g and a radial compression resistance of 7 kg, determined by means of a TBH 30 (Erweka) hardness tester.

Example 2 in Accordance with the Invention (Preparation of Catalytic Material Comprising Zeolite Beta)

The extruded catalytic material based on zeolite beta in acid form and bound with alumina is prepared as reported in Example 4 of EP 0 847 802.

1.9 g of sodium aluminate (56% $Al_2O_3$) were dissolved in 58.8 g of an aqueous solution of 40% by weight tetraethylammonium hydroxide. 58.4 g of demineralized water were added to the solution. The mixture was heated to 80% and stirring was continued until the complete dissolution of the powders. The clear solution thus obtained was mixed with 37.5 g of Ludox® HS 40 colloidal silica in a 40% by weight suspension. After mixing, a uniform gel having pH=14 was obtained, which was inserted into an AISI 316 steel autoclave equipped with an anchor stirrer. The gel was left to crystallize in hydrothermal conditions at 150° C. for about 10 days under static conditions and at autogenous pressure. At the end, after cooling, the solid phase was separated from the mother liquor from the suspension obtained by filtration. The aforementioned solid phase was subjected to washing with demineralized water.

The wet panel was dispersed again in an aqueous solution of ammonium acetate (200 g water and 16 g ammonium acetate) for ion exchange. The suspension was heated for an hour to 80° C. The suspension was then filtered and the solid obtained re-dispersed in demineralized water (150 mL) for washing. The suspension was re-filtered obtaining a wet panel of zeolite beta in ammonium/alkyl ammonium form. The aluminum content is 3.38%. The XRD analysis confirmed the presence of a single crystalline zeolite phase characteristic of the BEA structure, while the chemical analysis of the material allowed the SAR of the zeolite to be determined, which was 19 and the residual sodium content, which was 112 ppm. The material thus prepared, without being preliminarily calcinated, was extruded with pseudoboehmite as an alumina precursor and solutions of acetic acid as peptizing agents, as described in Example 4 of EP 0 847 802 obtaining a 50% zeolite material and a surface area of 482 m$^2$/g.

Example 3 (Comparative): (Preparation of Catalytic Material Comprising Zeolite Y)

The preparation is performed as reported in Example 1 of EP 1 572 357 B1.

260 g of commercial zeolite Y in ammonium form (CBV 712, Zeolyst International™) were mixed dry with 278 g of Versal™ V250 pseudoboehmite (UOP LLC) in a mixer for about 60 minutes.

At the end, 310 mL of a 0.5% by weight acetic acid solution were added over 36 minutes to the mixture of powders, while mixing constantly. After the addition, the pasty mixture was left to mix further at 400 rpm for 12 minutes, then unloaded from the mixer and transferred into an extruder and extruded in the form of rectangular pellets.

After drying in a ventilated oven at 25° C. for 48 hours the pellets of catalytic material were placed in a muffle furnace and calcinated in air atmosphere at a temperature programmed according to the following gradient: from room temperature to 120° C. in 6 hours; 120° C. constant for 2 hours; from 120° C. to 350° C. in 6 hours; 350° C. constant for 4 hours; from 350° C. to 550° C. in 4 hours; 550° C. constant for 8 hours.

The finished catalyst is in the form of rectangular pellets having an approximate length of 7 mm and approximate diameter of 2.1 mm.

Based on the weight loss at 550° C. measured on the starting components, an extrusion of zeolite and γ-alumina was obtained in a weight ratio of 50:50 in which the zeolite is in acid form. The material thus obtained has a surface area of 499 m$^2$/g.

Example 4 Comparative (Preparation of the Catalytic Material Based on Alumina)

A commercial bayerite (Versal™ B, UOP) was used, with high purity, high crystalline density and that provides catalytic compositions characterized by a high surface area after calcination and a higher acidity with respect to gamma aluminas. The calcination of the bayerite evolves through alumina phases with a high surface area, such as eta and theta. 1000 g of Versal™ B (UOP) were mixed with 500 mL of a 1% by weight acetic acid solution, over 60 minutes. After the addition, the pasty mixture was aged at ambient temperature for 24 hours, then transferred into a roller extruder equipped with a draw-plate with holes having a 2 mm diameter. The material was extruded in the form of pellets having a diameter of about 2 mm. The material was then calcinated in air atmosphere for 2 hours at 350° C. and subsequently for another 3 hours at 550° C. The material thus obtained has a surface area of 212 m$^2$/g.

Examples 5, 6, 7, 8, 9 in Accordance with the Invention (Catalytic Dehydration Test of 2-Propanol with Catalytic Material Comprising Zeolite ZSM-12 in Acid Form)

The dehydration tests of 2-propanol were performed using a tubular reactor 3 m long having a section of 2.98 mm$^2$, with vertical spiral insertion in a thermostated chamber with forced air circulation at controlled temperature and pressure.

About 10 g of catalytic material based on ZSM-12 zeolite in acid form, formed in the presence of an alumina-based binder, prepared in accordance with Example 1, were loaded into the reactor.

The tests were performed by feeding 2-propanol continuously to the reactor from the bottom upwards (upflow), using an HPLC pump.

The tests were performed at temperatures comprised between 200° C. and 205° C. and pressures comprised between 0.1 MPa and 0.2 MPa, in space velocity conditions (WHSV) comprised between 1 h$^{-1}$ and 2 h$^{-1}$.

The reaction effluent leaving the reactor is cooled in a glass column in whose outer jacket a fluid cooled to 5° C. flows. This column separates a liquid phase (mainly comprising water) and a gaseous phase (substantially comprising propylene), which passes into a glass manifold and then into a measuring instrument with a volumetric flow rate from which it is possible to measure the weight of the product.

The liquid phase collected on the bottom of the cooled glass column was taken for weighing and gas chromatography analysis, in a HP 6890 gas chromatograph equipped with a PONA column (50 m) and a flame ionization detector. For analyzing the liquid phase, 0.5 µl samples were used, in which methyl-ethyl-ketone were added as the internal standard.

For analyzing the gaseous phase, 0.5 ml samples of said gaseous phase, collected by the glass manifold, were subjected to gas chromatography analysis as described above.

The results of the tests are shown in Table 1 below.

TABLE 1

| Example | WHSV (h$^{-1}$) | Temperature (° C.) | Pressure (MPa) | 2-propanol conversion (%) | Selectivity to propylene (%) | Selectivity to ether (IPE) (%) | Selectivity to non-recoverable products (%) | Productivity kg$_p$/kg$_c$ | Operating time (hours) (h) |
|---|---|---|---|---|---|---|---|---|---|
| 5 | 2 | 200 | 0.1 | 99.3 | 98.3 | 0.01 | 1.65 | 228 | 168 |
| 6 | 2 | 200 | 0.1 | 99.2 | 99.0 | 0.01 | 0.97 | 422 | 312 |
| 7 | 1 | 200 | 0.1 | 99.6 | 97.9 | 0.01 | 2.10 | 439 | 550 |
| 8 | 2 | 200 | 0.1 | 99.1 | 99.7 | 0 | 0.32 | 758 | 814 |
| 9 | 2 | 205 | 0.1 | 99.6 | 99.4 | 0 | 0.63 | 1243 | 1008 |

The "non-recoverable" products conventionally comprise products that cannot be exploited to provide propylene, e.g. isobutane, acetone and olefins and C$_4$, C$_5$ and C$_6$ paraffins. Since isopropylether (IPE) is instead a product that can be recovered to provide propylene, it is not included in the "non-recoverable" products and therefore its selectivity is stated. The productivity is determined as the ratio between the weight of the desired product (kg$_p$) and the weight of the catalyst (kg$_c$).

The reaction was voluntarily stopped after 1008 hours of operation, in the absence of significant decay processes, in the absence of any yield reductions or flow rate losses. From Example 9 it can be deduced that by using catalytic material comprising zeolite ZSM-12 at a temperature equal to 205° C., pressure of 0.1 MPa and WHSV equal to 2 h$^{-1}$ a 99.6% conversion of 2-propanol and a 99.0% yield of propylene are obtained, with a selectivity of 99.4%, even after 1008 hours of operation and a total productivity of 1243 kg propylene for every kg of catalyst.

From the comparison between the data of Examples 5, 6, 8 the absence of significant decay processes is highlighted.

Examples 7 and 9 show that even when the space velocity and temperature are varied, within the claimed intervals, the aforementioned catalytic system can still be used with excellent results, even at higher operating times than the exemplified ones, although evidence of deactivation can start to be displayed.

The catalyst and the reaction conditions, according to the invention, are therefore applicable to industrial contexts, as well as being new and surprisingly efficient with respect to the catalysts described in the art.

Examples 10, 11, 12 in Accordance with the Invention (Catalytic Dehydration Test of 2-Propanol with Catalytic Material Comprising Zeolite Beta in Acid Form)

About 10 g of catalytic material based on zeolite beta in acid form, formed in the presence of an alumina-based binder, prepared in accordance with Example 2, were loaded into a reactor like the one used in Example 5 above.

The tests were performed as described above for Examples 5, 6 and 7, but at temperatures comprised between 185° C. and 200° C. and pressures comprised between 0.1 MPa and 1.5 MPa, in space velocity conditions (WHSV) comprised between 1 h$^{-1}$ and 2 h$^{-1}$.

The results of the tests are shown in Table 2 below.

TABLE 2

| Example | WHSV (h$^{-1}$) | Temperature (° C.) | Pressure (MPa) | 2-propanol conversion (%) | Selectivity to propylene (%) | Selectivity to ether (IPE) (%) | Selectivity to non-recoverable products (%) | Productivity kg$_p$/kg$_c$ | Operating time (hours) (h) |
|---|---|---|---|---|---|---|---|---|---|
| 10 | 2 | 200 | 1.5 | 93.8 | 97.4 | 0.46 | 2.18 | 188 | 148 |
| 11 | 2 | 200 | 0.1 | 99.5 | 99.0 | 0 | 0.98 | 552 | 408 |
| 12 | 1 | 185 | 0.1 | 97.6 | 99.3 | 0.04 | 0.67 | 814 | 670 |

Using catalytic material comprising zeolite beta in acid form at a temperature of 200° C., pressure of 0.1 MPa and WHSV of 2 h a 99.5% conversion of 2-propanol is obtained with 99.0% selectivity, even after 408 hours of operation (Example 11).

Variations to the operating conditions such as space velocity increases, pressure increases (Example 10) and temperature reductions (Example 12) may be managed by using appropriate combinations of the operating conditions themselves, within the claimed ranges, without substantially sacrificing the system performance levels.

The reaction was voluntarily stopped after 670 hours of operation, but in the absence of significant decay processes, in the absence of any yield reductions or flow rate losses.

It is important to note that it is possible to reduce the temperature to 185° C., maintaining the pressure equal to 0.1 MPa, and to obtain a satisfactory conversion value of 2-propanol (97.6%) at space velocity of 1 h, compatible values with industrial applications.

Comparative Examples 13, 14, 15 (Catalytic Dehydration Test of 2-Propanol with Catalytic Material Comprising Zeolite Y in Acid Form)

About 10 g of catalytic material based on zeolite Y in acid form, formed in the presence of an alumina-based binder, prepared in accordance with comparative Example 3, were loaded into a reactor like the one used in Example 5 above.

The tests were performed as described above for Examples 5, 6 and 7, but at a temperature of 200° C. and pressures comprised between 0.1 MPa and 1.5 MPa, in space velocity conditions (WHSV) equal to 2 h.

The results of the tests are shown in Table 3 below.

TABLE 3

| Example | WHSV ($h^{-1}$) | Temperature (° C.) | Pressure (MPa) | 2-propanol conversion (%) | Selectivity to propylene (%) | Selectivity to ether (IPE) (%) | Selectivity to non-recoverable products (%) | Productivity $kg_p/kg_c$ | Operating time (hours) (h) |
|---|---|---|---|---|---|---|---|---|---|
| 13 | 2 | 200 | 1.5 | 93.3 | 98.2 | 0.54 | 1.29 | 146 | 118 |
| 14 | 2 | 200 | 0.1 | 98.1 | 99.2 | 0.04 | 0.72 | 338 | 262 |
| 15 | 2 | 200 | 0.1 | 97.1 | 99.4 | 0.11 | 0.54 | 593 | 454 |

Using catalytic material comprising zeolite Y lower conversions of 2-propanol are obtained with respect to those obtained with catalytic materials comprising zeolite ZSM-12 or zeolite beta. Even if in some cases a satisfactory selectivity is obtained, especially at high pressure, these results are however not constant in the long term, highlighting lower stability as a function of the operating time. From the comparison between examples 6 and 8 no decay of the yield to 2-propanol is highlighted after a productivity of the ZSM-12 based catalyst of 336 kg/g, (−0.1% Conversion); from the comparison between examples 14 and 15 a decay of the yield to 2-propanol in the proximity of a percentage point is highlighted already after a productivity of the zeolite Y based catalyst of 255 $kg_p/kg_c$ (−1.0% conversion)

Comparative Examples 16 and 17 (Catalytic Dehydration Test of 2-Propanol with Catalytic Material Comprising Alumina)

About 10 g of alumina based catalytic material, prepared in accordance with the comparative Example 4, were loaded into the reactor.

The tests were performed as described for Examples 5, 6 and 7 in the operating conditions stated in Table 4.

TABLE 4

| Example | WHSV ($h^{-1}$) | Temperature (° C.) | Pressure (MPa) | 2-propanol conversion (%) | Selectivity to propylene (%) | Selectivity to ether (IPE) (%) | Selectivity to non-recoverable products (%) | Productivity $kg_p/kg_c$ | Operating time (hours) (h) |
|---|---|---|---|---|---|---|---|---|---|
| 16 | 0.7 | 242 | 0.1 | 61.6 | 70.0 | 29.9 | 0.10 | 21 | 96 |
| 17 | 2 | 290 | 0.1 | 99.8 | 99.8 | 0 | 0.17 | 525 | 774 |

From the comparative tests, the following is highlighted:

The state of the art is confirmed in the sense of the importance of operating at temperatures in the proximity of 300° C. with alumina based catalytic materials in order to obtain good conversions. At temperatures less than 240° C. good conversion values cannot be obtained, even at low space velocity (WHSV) values. Alumina starts to become significantly active at temperatures that are at least 50° C. higher than the reaction temperatures of catalysts containing zeolites. The catalytic contribution of the binding aluminas used in the examples according to the invention, under the stated operating conditions, can therefore be considered null or secondary.

Surprisingly, it has been demonstrated that the use of catalytic materials comprising MTW structure and BEA structure zeolites, such as zeolite ZSM-12 and zeolite beta, maintain high yields for suitable durations for industrial use, better than large pore zeolite Y, known in the art as one of the best catalysts for dehydrating ethanol (as described by T. K. Phung, L. Proietti Hernández, A. Lagazzo and G. Busca in "Dehydration of ethanol over zeolites, silica alumina and alumina: Lewis acidity, Brønsted acidity and confinement effects" (2015), *Appl. Catal. To: General*, vol. 493, pag. 77-89).

Finally, it is however to be understood that further changes and variations may be made to the process described and illustrated herein which do not depart from the scope of protection defined by the appended claims.

The invention claimed is:

1. Process for producing at least one olefin by dehydrating at least one alcohol having a number of carbon atoms comprised between 2 and 6, in the presence of a catalytic material comprising at least one large pore zeolite in acid form or predominantly in acid form selected from a zeolite having BEA structure, a zeolite having MTW structure and a mixture thereof, wherein said catalytic material includes at least one inorganic binder, which is carried out in the substantial absence of aromatic compounds, and separating said olefin from a product.

2. Process according to claim 1, wherein said alcohol is 2-propanol.

3. Process according to claim 1, wherein said zeolite has BEA structure.

4. Process according to claim 3, wherein said zeolite having BEA structure has a SAR in a range between 15 and 60.

5. Process according to claim 3, wherein said zeolite having BEA structure is a beta zeolite.

6. Process according to claim 1, wherein said zeolite has MTW structure.

7. Process according to claim 6, wherein said zeolite having MTW structure has a SAR in a range between 40 and 200.

8. Process according to claim 6, wherein said zeolite having MTW structure is a zeolite ZSM-12.

9. Process according to claim 1, wherein the olefin does not contain conjugated double bonds.

10. Process according to claim 1, wherein said olefin has the same number of carbon atoms as the starting alcohol.

11. Process according to claim 1, wherein said inorganic binder comprises at least one of silica, alumina, silico-alumina and mixtures thereof.

12. Process according to claim 1, wherein said inorganic binder is present in an amount that produces said catalytic material in which the ratio between zeolite and binder is in a range between 95:5 and 5:95.

13. Process according to claim 1, carried out at a temperature in a range between 100° C. and 300° C.

14. Process according to claim 1, carried out at a pressure in a range between 0.01 MPa and 2 MPa.

15. Process according to claim 1, conducted in a gaseous or liquid/gaseous phase.

16. Process according to claim 1, wherein the WHSV space velocity is in a range between 0.5 $h^{-1}$ and 10 $h^{-1}$.

17. Integrated phenol production process comprising the steps:
(a) converting 2-propanol as said alcohol to propylene as said separated olefin, by using the process according to claim 1;
(b) alkylating benzene with said propylene obtained in step (a) to obtain cumene, in the presence of a catalytic material comprising at least one large pore zeolite in acid form;
(c) oxidizing the cumene obtained in step (b) with the formation of cumyl hydroperoxide;
(d) treating the cumyl hydroperoxide obtained in step (c) with acid to obtain a mixture of phenol and acetone;
(e) separating said phenol from said acetone;
(f) hydrogenating said acetone separated in step (e) to obtain 2-propanol, which is at least partially recycled to step (a).

18. Process for producing at least one olefin by dehydrating at least one alcohol having a number of carbon atoms comprised between 2 and 6, in the presence of a catalytic material comprising at least one large pore zeolite in acid form or predominantly in acid form selected from a zeolite having BEA structure, a zeolite having MTW structure and a mixture thereof, said catalytic material including an extrusion of said large pore zeolite that is not calcined, an inorganic binder and a peptizing agent, and separating said olefin from a product.

* * * * *